United States Patent [19]
Morris et al.

[11] Patent Number: 5,932,764
[45] Date of Patent: Aug. 3, 1999

[54] IRIDIUM-CATALYZED CARBONYLATION PROCESS FOR THE PRODUCTION OF A CARBOXYLIC ACID

[75] Inventors: George Ernest Morris; John Glenn Sunley, both of Cottingham, United Kingdom

[73] Assignee: BP Chemicals Limited, United Kingdom

[21] Appl. No.: 08/984,996

[22] Filed: Dec. 4, 1997

[30] Foreign Application Priority Data

Dec. 5, 1996 [GB] United Kingdom .................. 9625335

[51] Int. Cl.⁶ ........................... C07C 51/12; C07C 51/14
[52] U.S. Cl. ............................................ 562/519; 562/520
[58] Field of Search ...................... 562/519, 520

[56] References Cited

U.S. PATENT DOCUMENTS

| | | | |
|---|---|---|---|
| 4,661,624 | 4/1987 | Chang et al. | 560/232 |
| 5,672,743 | 9/1997 | Garland et al. | 562/519 |
| 5,773,642 | 6/1998 | Denis et al. | 560/232 |

FOREIGN PATENT DOCUMENTS

| | | | |
|---|---|---|---|
| 1069262 | 2/1993 | China | C07C 53/08 |
| 0 055 618-A1 | 7/1982 | European Pat. Off. | C07C 51/12 |
| 0 161 874-A1 | 11/1985 | European Pat. Off. | C07C 53/08 |
| 0 441 260-A1 | 8/1991 | European Pat. Off. | C07C 51/12 |
| 0 350 635-B1 | 9/1993 | European Pat. Off. . | |
| 0 618 009-A1 | 10/1994 | European Pat. Off. | B01J 31/40 |
| 0 643 034 A1 | 3/1995 | European Pat. Off. . | |
| 0 685 446 A1 | 12/1995 | European Pat. Off. . | |
| 0685446 A1 | 12/1995 | European Pat. Off. . | |
| 2 155 929 | 10/1985 | United Kingdom | C07C 51/56 |
| 2 274 106 | 7/1994 | United Kingdom | C07C 51/12 |
| 2 315 069 | 1/1998 | United Kingdom . | |
| WO 96/14286 | 5/1996 | WIPO | C07C 51/12 |
| WO 96/14287 | 5/1996 | WIPO | C07C 51/12 |

*Primary Examiner*—Samuel Barts
*Assistant Examiner*—Rosalynd Keys
*Attorney, Agent, or Firm*—Morgan & Finnegan, L.L.P.

[57] ABSTRACT

A process for the production of a carboxylic acid having n+1 carbon atoms comprises (a) carbonylating with carbon monoxide in a first reaction zone at elevated temperature and pressure an alkyl alcohol having n carbon atoms and/or a reactive derivative thereof to produce a carboxylic acid having n+1 carbon atoms in a liquid reaction composition comprising carboxylic acid product, an iridium catalyst, an alkyl halide co-catalyst, water, an ester of the carboxylic acid product and the alkyl alcohol, and optionally one or more promoters, (b) withdrawing from the first reaction zone at least a portion of the liquid reaction composition together with dissolved and/or entrained carbon monoxide, and passing at least a portion of the withdrawn liquid reaction composition and carbon monoxide to a second reaction zone, ((c)reacting at least 1% of the dissolved and/or entrained carbon monoxide in the withdrawn reaction composition by further carbonylation at elevated temperature and pressure in the second reaction zone to produce further carboxylic acid product.

26 Claims, 4 Drawing Sheets

IRIDIUM-CATALYZED CARBONYLATION PROCESS FOR THE PRODUCTION OF A CARBOXYLIC ACID

The present invention relates to a process for the production of a carboxylic acid by the liquid phase carbonylation of an alkyl alcohol and/or a reactive derivative thereof in the presence of an iridium catalyst, an alkyl halide co-catalyst and optionally one or more promoters.

Carbonylation processes in the presence of iridium catalysts are known and are described, for example, in GB-A-1234121, US-A-3772380, DE-A-1767150, EP-A-0616997, EP-A-0618184, EP-A-0618183, EP-A-0643034, EP-A-0657386 and WO-A-95/31426. In the promoted process of EP-A-0643034 it is stated that ionic contaminants such as, for example, (a) corrosion metals, particularly nickel, iron and chromium and (b) phosphines or nitrogen-containing compounds or ligands which may quaternize in situ should be kept to a minimum in the liquid reaction composition as these will have an adverse effect on the reaction by generating $I^-$ in the liquid reaction composition which has a detrimental effect on the reaction rate.

In continuous liquid phase processes, a portion of the liquid reaction composition comprising a carboxylic acid, an iridium catalyst, an alkyl halide co-catalyst, water, an alkyl ester of the carboxylic acid, an optional promoter and residual carbon monoxide in dissolved and/or entrained state is withdrawn and product recovered therefrom by one or more flash and/or distillation stages.

EP-A-0685446 relates to a process for the preparation of acetic acid which comprises carbonylating, methanol with carbon monoxide in a first reactor in the presence of a rhodium catalyst. The reaction fluid containing dissolved carbon monoxide is passed from the first reactor to a second reactor where the dissolved carbon monoxide, without the feeding, of additional carbon monoxide, is further reacted before the reaction fluid is introduced into a flash zone. However, in this process the presence of iodide salts, for example, inorganic iodides such as lithium iodide or organic iodide salts such as a quaternary ammonium iodide is essential for maintaining the stability of the catalyst at low carbon monoxide partial pressures and/or water concentration, whereas iodide salts as mentioned hereinabove generally have an adverse effect upon the reaction rate for an iridium-catalyzed carbonylation process.

There remains the need for an improved process for the utilization of carbon monoxide in the liquid phase carbonylation of an alkyl alcohol and/or a reactive derivative thereof in the presence of an iridium catalyst, an alkyl halide co-catalyst, water and optionally one or more promoters.

According to the present invention there is provided a process for the production of a carboxylic acid having n+1 carbon atoms which process comprises (a) carbonylating with carbon monoxide in a first reaction zone at elevated temperature and pressure an alkyl alcohol having n carbon atoms and/or a reactive derivative thereof to produce a carboxylic acid having n +1 carbon atoms in a liquid reaction composition comprising carboxylic acid product, an iridium catalyst, an alkyl halide co-catalyst, water, an ester of the carboxylic acid product and the alkyl alcohol, and optionally one or more promoters, (b) withdrawing from the first reaction zone at least a portion of the liquid reaction composition together with dissolved and/or entrained carbon monoxide, and passing at least a portion of the withdrawn liquid reaction composition and carbon monoxide to a second reaction zone, (c) reacting at least 1% of the dissolved and/or entrained carbon monoxide in the withdrawn reaction composition by further carbonylation at elevated temperature and pressure in the second reaction zone to produce further carboxylic acid product.

Advantages arising from operating the process of the present invention include (i) an increase in the amount of carbon monoxide consumed resulting in a reduced flow of non-condensable (gases in the exit stream from the second reaction zone, and hence lower off-gas processing requirement and (ii) increased consumption of carbon monoxide and yield of acetic acid.

The process of the present invention solves the technical problem defined above by subjecting, liquid reaction composition withdrawn from a first reaction zone together with dissolved and/or entrained carbon monoxide to further conditions of elevated temperature and pressure to consume carbon monoxide and produce further carboxylic acid product.

In step (b) of the process of the present invention at least a portion of the liquid reaction composition together with dissolved and/or entrained carbon monoxide is withdrawn from the first reaction zone and at least a portion of the withdrawn liquid and dissolved and/or entrained carbon monoxide passed to a second reaction zone. Preferably substantially all the liquid reaction composition together with dissolved and/or entrained carbon monoxide withdrawn from the first reaction zone is passed to the second reaction zone.

The second reaction zone may be operated at a reaction temperature in the range 100 to 300° C., preferably in the range 150 to 230° C. The second reaction zone may be operated at a temperature higher than the first reaction zone, typically up to 30° C. higher. The second reaction zone may be operated at a reaction pressure in the range 10 to 200 barg, preferably in the range 15 to 100 barg. Preferably, the reaction pressure in the second reaction zone is equal to or less than the reaction pressure in the first reaction zone. The residence time of liquid reaction composition in the second reaction zone is suitably in the range 5 to 300 seconds, preferably 10 to 100 seconds.

There may be introduced to the second reaction zone carbon monoxide in addition to that introduced to the second reaction zone as dissolved and/or entrained carbon monoxide. Such additional carbon monoxide may be cojoined with the first liquid reaction composition prior to introduction to the second reaction zone and/or may be fed separately to one or more locations within the second reaction zone. Such additional carbon monoxide may contain impurities, such as for example $H_2$, $N_2$, $CO_2$ and $CH_4$. The additional carbon monoxide may be comprised of high pressure off-gas from the first reaction zone which could advantageously allow the first reaction zone to be operated at a higher CO pressure with the resulting higher flow of carbon monoxide being fed to the second reaction zone. Additionally it could eliminate the requirement for a high pressure off-gas treatment.

The additional carbon monoxide may also be comprised of another carbon monoxide-containing gas stream such as for example a carbon monoxide-rich stream from another plant.

An advantage of employing a second reaction zone is that carbon monoxide in a carbon monooxide-rich stream may be utilized in the second reaction zone without disturbing the operation of the first reaction zone.

Preferably greater than 10%, more preferably greater than 25%, even more preferably greater than 50%, for example at least 95%, of the dissolved and/or entrained carbon monoxide in the withdrawn reaction composition from the first reaction zone is consumed in the second reaction zone. Preferably to prevent a significant increase in the volatility of the iridium catalyst and/or optional promoter the amount of carbon monoxide in the second liquid composition withdrawn from the second reaction zone should not be reduced too low, typically to maintain at least 20% by volume of the dissolved and/or entrained gases therein and may be comprised of unreacted entrained and/or dissolved and/or additional carbon monoxide. This also helps to reduce by-product formation, for example methane.

According to one embodiment of the present invention the first and second reaction zones are maintained in separate reaction vessels with means for withdrawing from the first reaction vessel and passing to the second reaction vessel liquid reaction composition from the first reaction vessel with dissolved and/or entrained carbon monoxide. Such a separate second reaction vessel may comprise a section of pipe between the first reaction vessel and a liquid reaction composition flashing valve. Preferably the pipe is liquid full. Typically the pipe's length to diameter ratio may be about 12:1, though length to diameter ratios both higher and lower than this may be employed. Alternatively, in such an embodiment, the first reaction vessel may be operated as a liquid-full back mixed reactor in fluidic communication with the second reaction vessel which may be operated as a bubble column reactor with limited back mixing.

The design of the second reaction zone is suitably such as to minimize or substantially eliminate back-mixing in the second reaction zone, which design would not be fulfilled by a stirred tank reactor.

In another embodiment of the present invention the second reaction zone may comprise of a relatively quiescent reaction zone within a reactor in the main body of which is maintained the first reaction zone. Such an arrangement may comprise, for example, a reactor partitioned into a first reaction zone forming a major proportion of the reactor space and having agitation means therein and a second smaller reaction zone having no agitation means, the second reaction zone being in liquid communication with the first reaction zone.

The first reaction zone may comprise a conventional liquid-phase carbonylation reaction zone. The pressure of the carbonylation reaction in the first reaction zone is suitably in the range 15 to 200 barg, preferably 15 to 100 barg, more preferably 15 to 50 barg and yet more preferably 18 to 35 barg. The temperature of the carbonylation reaction in the first reaction zone is suitably in the range 100 to 300 ° C., preferably in the range 150 to 220 ° C.

In the process of the present invention the carboxylic acid product comprises a $C_2$ to $C_{11}$, carboxylic acid, preferably a $C_2$ to $C_6$ carboxylic acid, more preferably a $C_2$ to $C_3$ carboxylic acid and most preferably is acetic acid.

Preferably, the alkyl alcohol carbonylation reactant is a primary or secondary alkyl alcohol, more preferably a primary alcohol. Suitably, the alkyl alcohol has 1 to 10 carbon atoms, preferably 1 to 5 carbon atoms, more preferably 1 to 2 carbon atoms and is most preferably methanol. Suitable reactive derivatives of the alkyl alcohol include the ester of the alcohol and the carboxylic acid product, for example methyl acetate, the corresponding, dialkyl ether, for example dimethyl ether; and the corresponding alkyl halide, for example methyl iodide. Water is required as co-reactant for ether or ester reactants. A mixture of alkyl alcohol and reactive derivatives thereof may be used as reactants in the process of the present invention for example a mixture of methanol and methyl acetate. Preferably, methanol and/or methyl acetate are used as reactants.

At least some of the alkyl alcohol and/or reactive derivative thereof will be converted to, and hence present as, the corresponding ester with the carboxylic acid product in the liquid carbonylation reaction composition by reaction with the carboxylic acid product or solvent. Preferably, the concentrations of alkyl ester in the liquid reaction compositions in the first and second reaction zones are independently in the range 1 to 70% by weight, more preferably 2 to 50% by weight, most preferably 3 to 35% by weight Water may be formed in situ in the liquid reaction compositions, for example, by the esterification reaction between alkyl alcohol reactant and carboxylic acid product. Water may be introduced independently to the first and second carbonylation reaction zones together with or separately from other components of the liquid reaction compositions. Water may be separated from other components of reaction compositions withdrawn from the reaction zones and may be recycled in controlled amounts to maintain the required concentration of water in the liquid reaction compositions. Preferably, the concentrations of water in the liquid reaction compositions in the first and second reaction zones are independently in the range 0.1 to 20% by weight, more preferably 1 to 15% by weight, yet more preferably 1 to 10% by weight.

Preferably, the alkyl halide in the carbonylation reaction has an alkyl moiety corresponding to the alkyl moiety of the alkyl alcohol reactant. Most preferably, the alkyl halide is methyl halide. Preferably, the alkyl halide is an iodide or bromide, most preferably an iodide. Preferably, the concentrations of alkyl halide in the liquid carbonylation reaction compositions in the first and second reaction zones are independently in the range 1 to 20% by weight, preferably 2 to 16% by weight.

The iridium catalyst in the liquid reaction compositions in the first and second reaction zones may comprise any iridium-containing compound which is soluble in the liquid reaction compositions. The iridium catalyst may be added to the liquid reaction compositions in any suitable form which dissolves in the liquid reaction compositions or is convertible to a soluble form. Preferably the iridium may be used as a chloride free compound such as acetates which are soluble in one or more of the liquid reaction composition components, for example water and/or acetic acid and so may be added to the reaction as solutions therein. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)_{I3}(CO)_2]^-H+$, $Ir_4(CO)_{12}$, $IrCl_3 4H_2O$, $IrBr_3 4H_2O$, $Ir_3(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $H_2[IrCl_6]$, preferably, chloride-free complexes of iridium such as acetates, oxalates and acetoacetates.

Preferably, the concentrations of the iridium catalyst in the liquid reaction compositions of the first and second reactors are independently in the range 100 to 6000 ppm by weight of iridium.

Preferably, the liquid reaction compositions in the first and second reaction zones additionally comprises as promoter one or more of osmium, rhenium, ruthenium, cadmium, mercury, zinc, gallium, indium and tungsten and are more preferably selected from ruthenium and osmium and most preferably is ruthenium. The promoter may comprise any promoter metal-containing compound which is soluble in the liquid reaction compositions. The promoter may be added to the liquid reaction compositions in any suitable form which dissolves in the liquid reaction compositions or is convertible to soluble form. Preferably, the promoter compound may be used as chloride-free compounds such as acetates which are soluble in one or more of the liquid reaction composition components, for example water and/or acetic acid and so may be added to the reaction as solutions therein.

Examples of suitable ruthenium-containing compounds which may be used include ruthenium (III) chloride, ruthenium (III) chloride trihydrate, ruthenium (IV) chloride, ruthenium (III) bromide, ruthenium (III) iodide, ruthenium metal, ruthenium oxides, ruthenium (III) formate, [Ru(CO)$_3$I$_3$]$^-$H$^+$, tetra(aceto)chlororthenium(II,III), ruthenium (III) acetate, ruthenium (III) propionate, ruthenium (III) butyrate, ruthenium pentacarbonyl, triruthenium­dodecacarbonyl and mixed ruthenium halocarbonyls such as dichlorotricarbonylruthenium (II) dimer, dibromotricarbonylruthenium (II) dimer, and other organoruthenium complexes such as tetrachlorobis(4- cymene)diruthenium(II), tetrachlorobis (benzene)diruthenium(II), dichloro(cycloocta-1,5-diene) ruthenium (II) polymer and tris(acetylacetonate)ruthenium (III).

Examples of suitable osmium-containing compounds which may be used include osmium (III) chloride hydrate and anhydrous, osmium metal, osmium tetraoxide, triosmiumdodecacarbonyl, pentachlro-$\mu$-nitrododiosmium and mixed osmium halocarbonyls such as tricarbonyldichloroosmium (II) dimer and other organoosmium complexes.

Examples of suitable rhenium-containing compounds which may be used include Re$_2$(CO)$_{10}$, Re(CO)$_5$Cl, Re(CO)$_5$Br, Re(CO)$_5$I, ReCL$_3$xH$_2$O ReCl$_5$yH$_2$O and [{ReCO)$_4$I}$_2$].

Examples of suitable cadmium-containing compounds which may be used include Cd(OAc)$_2$, CdI$_2$, CdBr$_2$, CdCl$_2$, Cd(OH)$_2$, and cadmium acetylacetonate.

Examples of suitable mercury-containing compounds which may be used as sources of co-promoter include Hg(OAc)$_2$, HgI$_2$, HgBr$_2$, HgCl$_2$, Hg$_2$I$_2$, and Hg$_2$Cl$_2$.

Examples of suitable zinc-containing, compounds which may be used as sources of co-promoter include Zn(OAc)$_2$, Zn(OH)$_2$, ZnI$_2$, ZnBr$_2$, ZnCl$_2$, and zinc acetylacetonate.

Examples of suitable (gallium-containing compounds which may be used as sources of co-promoter include galliuim acetylacetonate, gallium acetate, GaCl$_3$, GaBr$_3$, GaI$_3$, Ga$_2$Cl$_4$ and Ga(OH)$_3$.

Examples of suitable indium-containing compounds which may be used as sources of co-promoter include indium acetylacetonate, indium acetate, InCl$_3$, InBr$_3$, InI$_3$, Inl and In(OH)$_3$.

Examples of suitable tungsten-containing compounds which may be used as sources of co-promoter include W(CO)$_6$, WCl$_4$, WCl$_6$, WBr$_5$, WI$_2$, or C$_9$HI$_2$, W(CO)$_3$ and any tungsten chloro-,bromo- or iodo-carbonyl compound.

Preferably, the promoter-containing compounds are free of impurities which provide or generate in-situ ionic iodides which may inhibit the reaction, for example, alkali or alkaline earth metal or other metal salts.

Preferably, the promoter is present in an effective amount up to the limit of its solubility in the liquid reaction compositions and/or any liquid process streams recycled to the carbonylation reaction zones from the acetic acid recovery stage.

The promoter is suitably present in the liquid reaction compositions at a molar ratio of each promoter (when present): iridium in the range [0.1 to 100]:1, preferably [greater than 0.5]:1, more preferably [greater than 1]:1 and preferably [up to 20]:1 more preferably [up to 15]:1 and yet more preferably [up to 10]:1. The beneficial effect of a promoter such as ruthenium has been found to be greatest at the water concentration which gives the maximum carbonylation rate at any defined methyl acetate and methyl iodide concentration. A suitable promoter concentration is 400 to 5000 ppm.

Carboxylic acid may be used as a solvent for the carbonylation reaction.

Although in general it is preferred to operate the process in the substantial absence of added iodide salt, i.e. a salt generating, or dissociating an iodide ion, it may be possible under certain conditions to tolerate such a salt. Accordingly, ionic contaminants such as, for example, (a) corrosion metals, particularly nickel, iron and chromium and (b) phosphines or nitrogen-containing compounds or ligands which may quaternize in situ, should be kept to a minimum or eliminated in the liquid reaction composition as these may generally have an adverse effect on the reaction by generating I$^-$ in the liquid reaction composition which has an adverse effect on the reaction rate. Some corrosion metal contaminants such as for example molybdenum have been found to be less susceptible to the generation of I$^-$.

Corrosion metals which have all adverse effect on the reaction rate may be minimized by using suitable corrosion resistant materials of construction. Similarly, contaminants such as alkali metal iodides, for example lithium iodide, should be kept to a minimum. Corrosion metal and other ionic impurities may be reduced by the use of a suitable ion exchange resin bed to treat the reaction composition, or preferably a catalyst recycle stream. Such a process is described in U.S. Pat. No. 4007130.

Preferably, ionic contaminants are kept below a concentration at which they would generate less than 500 ppm I$^-$, preferably less than 250 ppm I$^-$ in the liquid reaction composition, more preferably less than 50 ppm I$^-$.

The carbon monoxide reactant for the carbonylation reactions may be essentially pure or may contain inert impurities such as carbon dioxide, methane, nitrogen, noble gases, water and C$_1$to C$_4$ paraffinic hydrocarbons. The presence of hydrogen in the carbon monoxide and generated in situ by the water gas-shift reaction is preferably kept low, for example, less than 1 bar partial pressure, as its presence may result in the formation of hydrogenation products. The partial pressure of carbon monoxide in the first and second reaction zones are suitably independently in the range 1 to 70 bar, preferably 1 to 35 bar and more preferably 1 to 15 bar.

Carboxylic acid product may be recovered from the second reaction zone and optionally together with or separately from the first reaction zone by flash separation. In flash separation liquid reaction composition is passed to a flashing zone via a flashing, valve. The flash separation zone may be an adiabatic flash vessel or may have additional heating means. In the flash separation zone a liquid fraction comprising the majority of the iridium catalyst and the majority of the optional promoters is separated from a vapour fraction comprising carboxylic acid, carbonylatable reactant, water and alkyl halide carbonylation co-catalyst; the liquid fraction being recycled to the first reaction zone and the vapour fraction being passed to one or more distillation zones. In the distillation zones carboxylic acid product is separated from other components which are recycled to the first and/or second reaction zones.

The carboxylic acid produced by the process according to the present invention may be further purified by conventional processes, for example further distillation to remove impurities such as water, unreacted carbonylation reactant and/or ester derivative thereof and higher-boiling, carboxylic acid by-products.

BRIEF DESCRIPTION OF DRAWINGS

The invention will now be illustrated by way of the following Examples and by reference to the accompanying FIGS.

Figure 3:
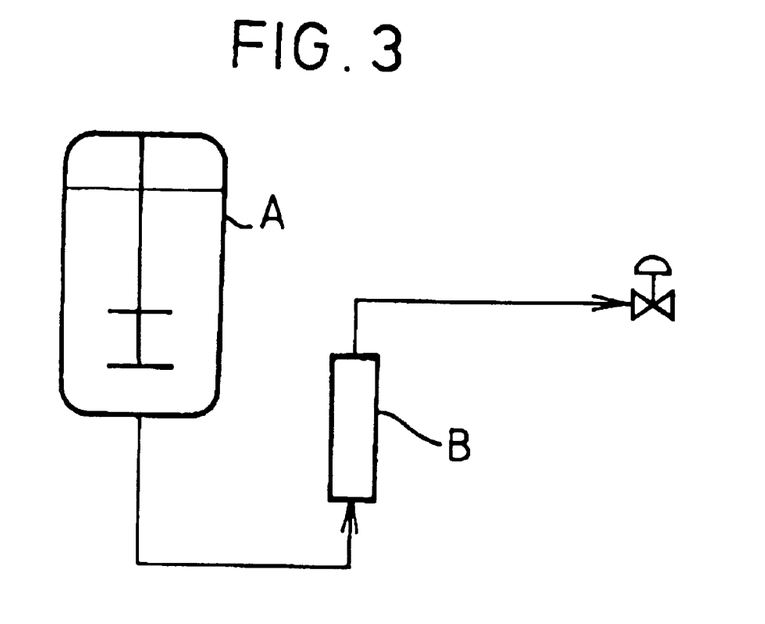
FIGS. 3 to 5 are representations of different arrangements of secondary reaction zones.

With reference to FIG. 3, A is a first reaction zone comprising a primary reactor incorporating an agitator and/ or jet mix and/or other means of agitation and B is a second reaction zone comprising a tubular (or pipe) secondary reactor in communication with a flashing valve.

Figure 4:
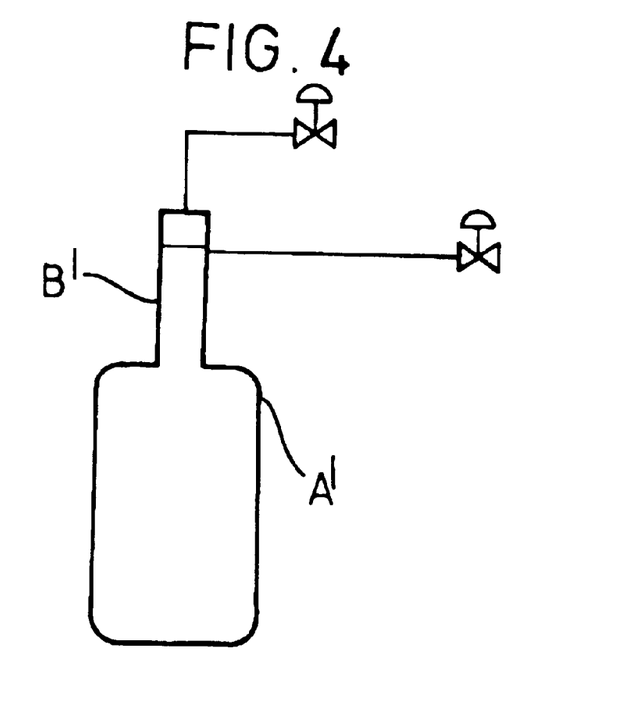

With reference to FIG. 4, A' is a first reaction zone comprising a primary reactor operated liquid full and incorporating an agitator and/or jet mix and/or other means of agitation. B' is a second reaction zone comprising a tubular (or pipe) secondary reactor mounted atop the primary reactor. The secondary reactor may be operated partially full of liquid with the liquid-filled portion in communication with a flashing valve and the gaseous space in communication with a high pressure off-gas valve (as shown). Alternatively, the secondary reactor may be operated liquid-full, thereby eliminating the need for a high pressure off-gas system.

Figure 5:
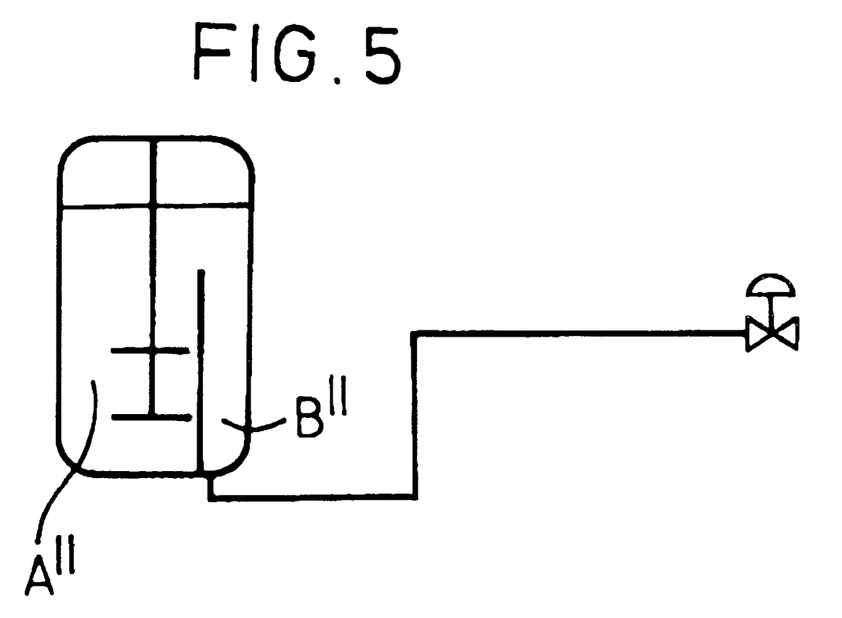

With reference to FIG. 5, A" is a first reaction zone comprising a primary reactor incorporating an agitator and/ or jet mix and/or other means of agitation. B" is a second reaction zone comprising a partitioned portion of the first reaction zone and in liquid communication therewith. The partitioned portion B" communicates with a flashing valve.

EXAMPLES

Example 1

Apparatus and Method

Figure 1:
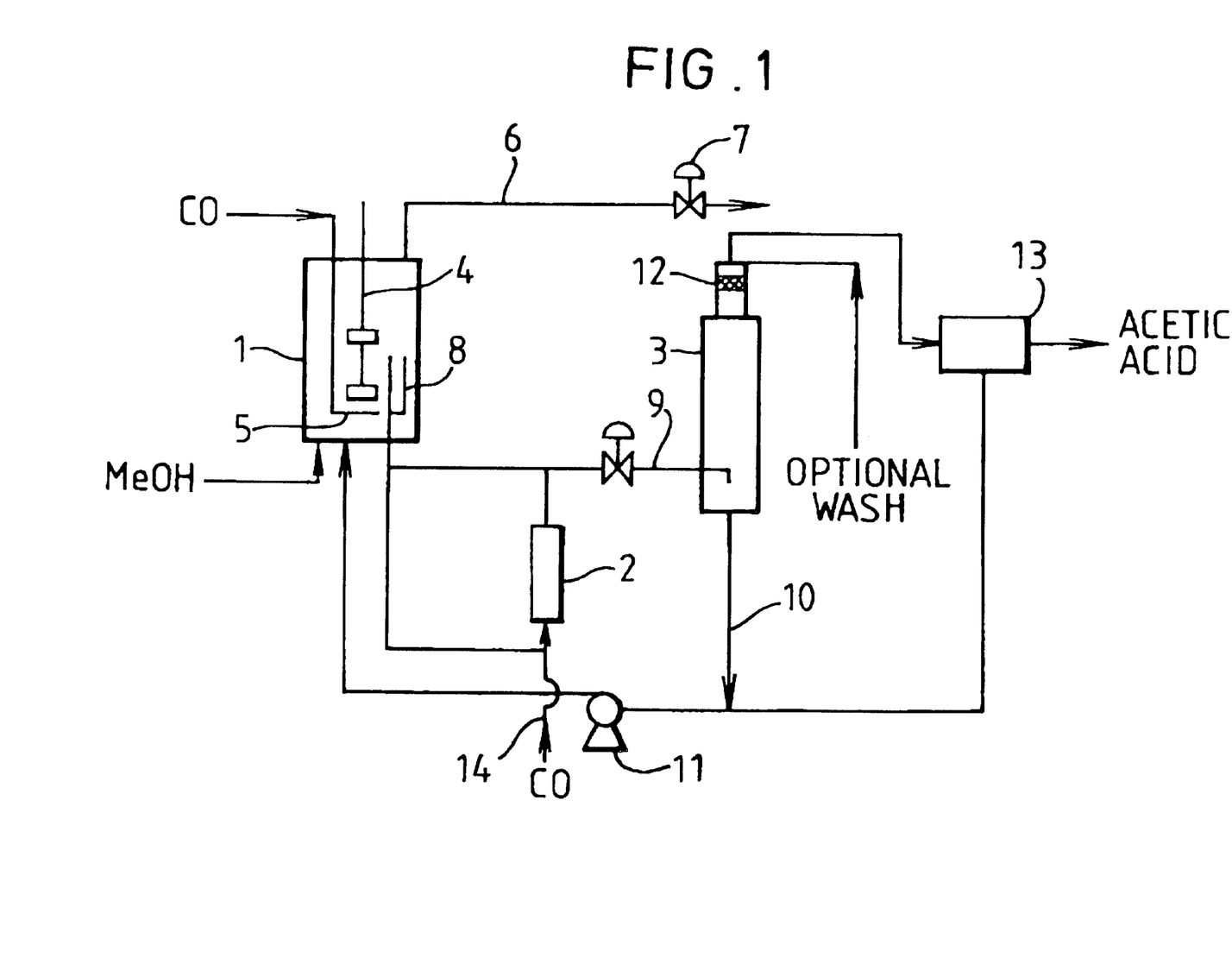
FIGS. 1 and 2 are schematic diagrams of the apparatus used in the Examples.
Figure 2:
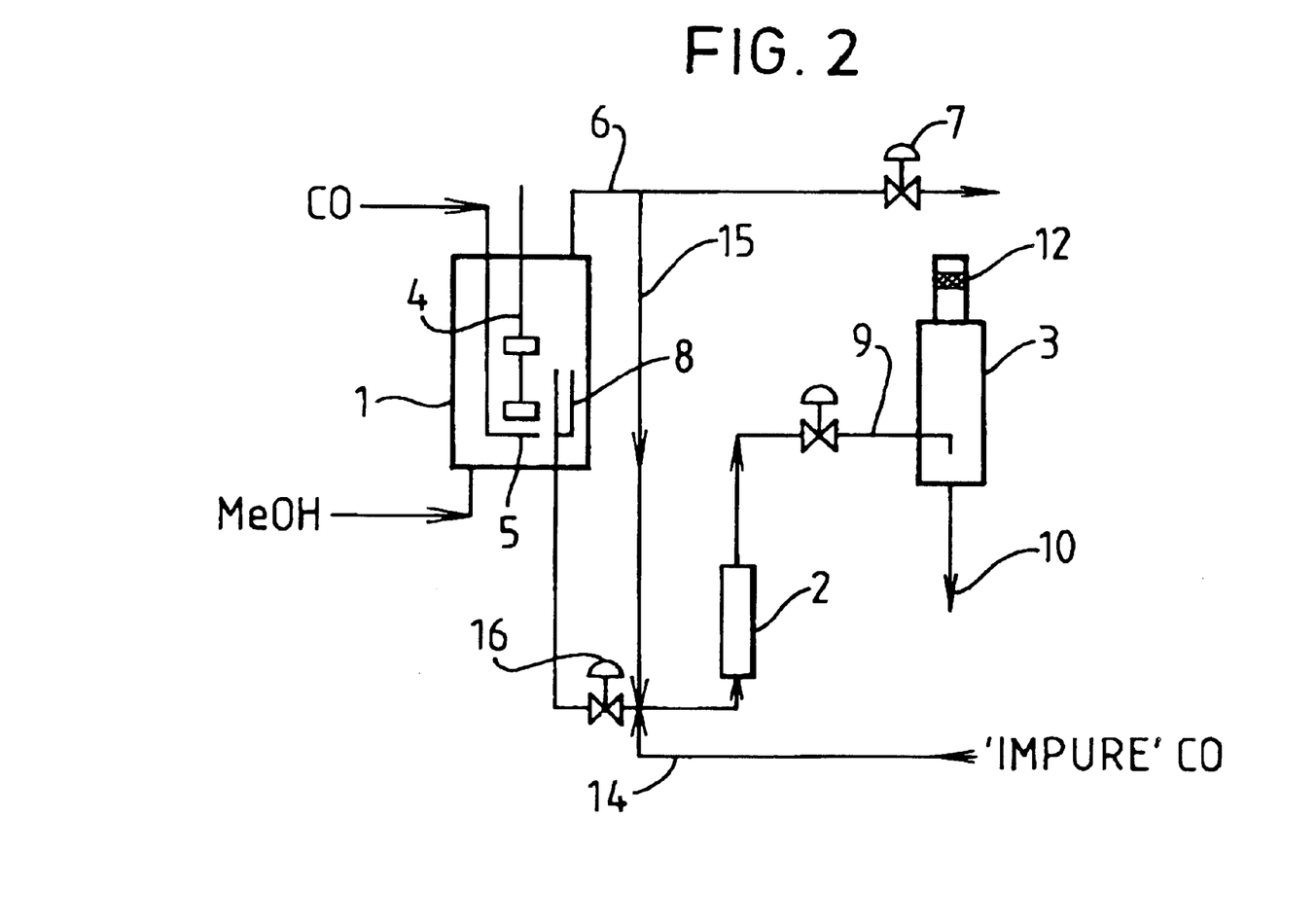

The apparatus used is shown in FIGS. 1 and 2. With reference to FIG. 1 the apparatus comprised a stirred primary carbonylation reactor (1), a secondary carbonylation reactor (2), a flash tank (3) and a purification system (not shown), all constructed from zirconium 702.

In use, commercial grade methanol, which has been used to scrub the off- gas is carbonylated in the 6 litre reactor (1) in the presence of the iridium carbonylation catalyst and promoter at a pressure of 24–32 barg and a temperature of 181–195° C. The reactor (1) is fitted with a stirrer/propeller (4) and a baffle cage (not shown) to ensure intimate mixing of the liquid and gaseous reactants. Carbon monoxide is supplied from a commercial plant, or from pressure bottles, to the reactor via a sparge (5) fitted beneath the stirrer (4). To minimize iron ingress into the reactor the carbon monoxide is passed through a carbon filter (not shown). A jacket (not shown), through which the hot oil is circulated, enables the reaction liquid in the reactor to be maintained at a constant reaction temperature. The liquid reaction composition is analyzed by near infra red analysis or by gas chromatography.

To purge inerts, high pressure off-gas is removed from the reactor through line (6). It is passed through a condenser (not shown) before the pressure is dropped to 1.48 barg across valve (7) for it to be fed into the scrubbing system.

Liquid reaction composition is withdrawn from the carbonylation reactor (1) down a still well (8) via line (9) into the flash tank (3) under reactor level control. In the flash tank the liquid reaction composition is flashed down to a pressure of 1.48 barg. The resulting mixture of vapour and liquid is separated; the catalyst-rich liquid is returned to the reactor by line (10) and pump (11) and the vapour is passed through a demister (12) and then directly into the acetic acid recovery system (13) as vapour.

The secondary reactor (2) is attached to the flashing line (9) and fitted with isolation valves such that the flow exiting the reactor either passes directly to the flashing valve or directly through the secondary reactor (2) to the flashing valve. The second reactor (2) comprises a pipe of diameter 2.5cm, length 30 cm and together with associated pipework has a volume of approximately 1 1% of the first reactor. The pipe is placed in parallel to the flashling line (9), and is provided with a supply of additional carbon monoxide via line 14. The secondary reactor is operated at the same pressure as the primary reactor.

Acetic acid is recovered from the vapour entering the acetic acid recovery system (13).

With reference to FIG. 2, the apparatus incorporates features 1 to 14 of FIG. 1 and additionally incorporates line 15 and control valve 16 (secondary reactor by-pass line not shown for clarity). The modification is necessary to enable high pressure (HP) offgas to be fed directly into the second reaction zone. Alternatively a compressor may be employed to feed the HP offgas to tile second reaction zone. Primarily this was to allow tile second reaction zone to operate at a pressure less than that of the first reaction zone. The CRS line to the reactor, including pump (11) have not been shown to aid clarity.

Example 1

Using the apparatus and method described with reference to FIG. 1 methanol was carbonylated in the primary carbonylation reactor (1) at 192.8° C. and a total pressure of 30.9 barg. A liquid reaction composition was withdrawn from the reactor through line (9). The liquid reaction composition in the primary reactor (1) comprised approximately 7% by weight of methyl iodide, 15% by weight of methyl acetate, 5% by weight of water, approx. 73% by weight of acetic acid, 1180 ppm of iridium and 1640 ppm ruthenium. Then, the liquid reaction composition withdrawn from the reactor was diverted into the second reactor (2). The liquid reaction composition was further carbonylated in the second reactor at a mid temperature of 190° C. and a total pressure of 30.9 barg with a residence time of 40–50 seconds.

The liquid reaction composition from the second reactor (2) was passed to the flash separation vessel (3) operated at a pressure of 1.48 barg. The results are shown in Table 1. The results show that 63 g/hr carbon monoxide was converted in the second reaction zone, which is a significant proportion (about 93%) of the 68 g/hr carbon monoxide estimated from a base line experiment to be dissolved and/or entrained in the first liquid reaction composition.

Example 2

The process of Example 1 was repeated except that the mid-temperature in the second reactor was maintained at 185° C. The results are shown in Table 1. This Example shows that dissolved and/or entrained CO in the liquid composition is consumed at 185° C.

Example 3

The process of Example 1 was repeated except that no external heat was supplied to the second reactor. The results are shown in Table 1. This Example shows that dissolved and/or entrained CO in the liquid composition is consumed in the absence of external heat.

Example 4

The process of Example 1 was repeated except that additional carbon monoxide (containing <2% v/v impurities) was fed to the second reactor at 35 g/hr. The results are shown in Table 1. This Example shows that dissolved and/or entrained CO in the liquid composition and additional CO feed is consumed at 190° C.

Example 5

The process of EXAMPLE 1 was repeated except that additional carbon monoxide (containing <2% v/v impurities) was fed to the second reactor at 65 g/hr. The restilts are shown in Table 1. This Example shows that dissolved and/or entrained CO in the liquid composition and additional CO feed is consumed at 190° C.

Example 6

The process of Example 1 was repeated except that additional carbon monoxide (containing <2% v/v impurities) was fed to the second reactor at 100 g/hr. The results are shown in Table 1. This Example shows that dissolved and/or entrained CO in the liquid composition and additional CO feed is consumed at 190° C.

TABLE 1

|  | Ex 1 | Ex 2 | Ex 3 | Ex 4 | Ex 5 | Ex 6 |
|---|---|---|---|---|---|---|
| Temp. of second reaction zone ° C. mid-temperature | 190 | 185 | * | 190 | 190 | 190 |
| Additional CO feed g/hr | 0 | 0 | 0 | 35 | 65 | 100 |
| CO converted in second reaction zone g/hr | 63 | 60 | 51 | 93 | 112 | 127 |
| First reactor temperature (° C.) | 192.8 | 187.5 | 191.7 | 191.6 | 191.4 | 191.6 |
| First reactor pressure (Barg) | 30.9 | 28.8 | 29.1 | 29.5 | 29.4 | 29.9 |

*not reported.

Examples 7 to 11

The primary reactor (1) was operated at a total pressure of 27.6 barg. The second reaction zone (2) was operated at a pressure of 27.0 barg using control valve (16). This pressure differential was the driving force which allowed HP offgas to be fed down the line (15) into tile second reaction zone. The temperature in the second reaction zone was controlled in a similar manner as for Example 4–6. The liquid reactor composition in the primary reactor 1 was similar to that for Examples 1 to 6, i.e. 5 wt% water, 7 wt% methyl iodide, and 15 wt% methyl acetate. The iridium and ruthenium concentrations were as shown in Table 2.

Example 7 was a repeat of Example 1, but in this case it was estimated that the amount of carbon monoxide dissolved and/or entrained in the liquid reaction composition withdrawn from the primary reactor (1) was 114 g/h. In Example 7 there was 91% carbon monoxide conversion in the second reaction zone. In Examples 8 to 10 varying amounts of HP offgas were directed into the second reaction zone (2) through line (15). The concentration of carbon monoxide in this stream was approximately 75% v/v for each Example.

Example 11 was designed to determine the effects of feeding impure carbon monoxide into the second reaction zone (2). This stream contained 70% v/v carbon monoxide, 25% v/v nitrogen and 5% v/v hydrogen.

The results of Examples 7 to 11 are given in Table 2.

TABLE 2

|  | Example 7 | Example 8 | Example 9 | Example 10 | Example 11 |
|---|---|---|---|---|---|
| HP Offgas feed (g/hr) | 0 | 56 | 19 | 121 | 0 |
| Additional feed (g/hr) | 0 | 0 | 0 | 0 | 175 |
| CO converted (g/hr) | 104 | 148 | 123 | 171 | 167 |
| Primary reactor temperature (° C.) | 187.2 | 186.8 | 187.3 | 187.5 | 188.8 |
| Reactor [Ir] (ppm) | 1230 | 1190 | 1180 | 1180 | 1130 |
| Reactor [Ru] (ppm) | 1660 | 1550 | 1560 | 1560 | 1530 |

We claim:

1. A process for the production of a carboxylic acid having n+1 carbon atoms which process comprises (a) carbonylating with carbon monoxide in a first reaction zone at elevated temperature and pressure an alkyl alcohol having n carbon atoms and/or a reactive derivative thereof to produce a carboxylic acid having n+1 carbon atoms in a liquid reaction composition comprising carboxylic acid product, an iridium catalyst, an alkyl halide co-catalyst, water, an ester of the carboxylic acid product and the alkyl alcohol, and optionally one or more promoters, (b) withdrawing from the first reaction zone at least a portion of the liquid reaction composition together with dissolved and/or entrained carbon monoxide, and passing at least a portion of the withdrawn liquid reaction composition and carbon monoxide to a second reaction zone, (c) reacting at least 1% of the dissolved and/or entrained carbon monoxide in the withdrawn reaction composition by further carbonylation at elevated temperature and pressure in the second reaction zone while keeping the added ionic iodide salt concentration in the reaction composition at less than 500 ppm I⁻ to produce further carboxylic acid product.

2. A process according to claim 1 wherein substantially all the liquid reaction composition together with dissolved and/or entrained carbon monoxide withdrawn from the first reaction zone is passed to the second reaction zone.

3. A process according to claim 1 wherein methanol and/or methyl acetate are carbonylated with carbon monoxide in the first reaction zone.

4. A process according to claim 1 wherein the concentrations of the ester of the carboxylic acid product and the alkyl alcohol in the first and second reaction zones are independently in the range from 3 to 35% by weight.

5. A process according to claim 1 wherein the concentrations of water in the liquid reaction compositions in the first and second reaction zones are independently in the range from 1 to 10% by weight.

6. A process according to claim 1 wherein the concentrations of alkyl halide in the liquid reaction compositions in the first and second reaction zones are independently in the range from 2 to 16% by weight.

7. A process according to claim 1 wherein the concentrations of the iridium catalyst in the liquid reaction compositions of the first and second reactors is in the range from 100 to 6000 ppm by weight of iridium.

8. A process according to claim 1 wherein the liquid reaction compositions additionally comprise as promoter one or more of ruthenium and osmium.

9. A process according to claim 8 wherein the promoter is present in the liquid reaction compositions at a molar ratio of each promoter to iridium of up to 10:1.

10. A process according to claim 1 when operated in the absence of added iodide salt.

11. A process according to claim 1 wherein in the first reaction zone the temperature of the carbonylation reaction is in the range 150 to 220° C. and the pressure is in the range 15 to 50 barg.

12. A process according to claim 1 wherein in the second reaction zone the reaction temperature is in the range 150 to 230° C. and the pressure is in the range 15 to 100 barg.

13. A process according to claim 1 wherein the residence time of liquid reaction composition in the second reaction zone is in the range 5 to 300 seconds.

14. A process for the production of a carboxylic acid having n+1 carbon atoms which process comprises (a) carbonylating with carbon monoxide in a first reaction zone at elevated temperature and pressure an alkyl alcohol having n carbon atoms and/or a reactive derivative thereof to produce a carboxylic acid having n+1 carbon atoms in a liquid reaction composition comprising carboxylic acid product, an iridium catalyst, an alkyl halide co-catalyst, water, an ester of the carboxylic acid product and the alkyl alcohol, and optionally one or more promoters, (b) withdrawing from the first reaction zone at least a portion of the liquid reaction composition together with dissolved and/or entrained carbon monoxide, and passing at least a portion of the withdrawn liquid reaction composition and carbon monoxide to a second reaction zone, (c) reacting at least 1% of the dissolved and/or entrained carbon monoxide in the withdrawn reaction composition by further carbonylation at elevated temperature and pressure in the second reaction zone to produce further carboxylic acid product, wherein there is introduced to the second reaction zone carbon monoxide in addition to that introduced to the zone as dissolved and/or entrained carbon monoxide.

15. A process according to claim 14 wherein the additional carbon monoxide is high pressure offgas from the first reaction zone.

16. A process according to claim 1 wherein greater than 25% of the dissolved and/or entrained carbon monoxide in the withdrawn reaction composition from the first reaction zone is consumed in the second reaction zone.

17. A process according to claim 1 wherein at least 95% of the dissolved and/or entrained carbon monoxide in the withdrawn reaction composition from the first reaction zone is consumed in the second reaction zone.

18. A process for the production of a carboxylic acid having n+1 carbon atoms which process comprises (a) carbonylating with carbon monoxide in a first reaction zone at elevated temperature and pressure an alkyl alcohol having n carbon atoms and/or a reactive derivative thereof to produce a carboxylic acid having n+1 carbon atoms in a liquid reaction composition comprising carboxylic acid product, an iridium catalyst, an alkyl halide co-catalyst, water, an ester of the carboxylic acid product and the alkyl alcohol, and optionally one or more promoters, (b) withdrawing from the first reaction zone at least a portion of the liquid reaction composition together with dissolved and/or entrained carbon monoxide, and passing at least a portion of the withdrawn liquid reaction composition and carbon monoxide to a second reaction zone, (c) reacting at least 1% of the dissolved and/or entrained carbon monoxide in the withdrawn reaction composition by further carbonylation at elevated temperature and pressure in the second reaction zone to produce further carboxylic acid product, wherein a second liquid composition is withdrawn from the second reaction zone and the amount of carbon monoxide in said second liquid composition is reduced to maintain at least 20% by volume of the dissolved and/or entrained gases therein and is comprised of unreacted and/or dissolved and/or additional carbon monoxide.

19. A process according to claim 1 wherein the first and second reaction zones are maintained in separate reaction vessels with means for withdrawing from the first reaction vessel and passing to the second reaction vessel liquid reaction composition from the first reaction vessel with dissolved and/or entrained carbon monoxide.

20. A process according to claim 19 wherein the second reaction vessel comprises a section of pipe between the first reaction vessel and a liquid reaction composition flashing valve.

21. A process according to claim 19 wherein the first reaction vessel is operated as a liquid-full back mixed reactor in fluidic communication with the second reaction vessel.

22. A process according to claim 21 wherein the second reactor is operated as a bubble column reactor with limited back mixing.

23. A process according to claim 1 wherein the second reaction zone comprises a relatively quiescent reaction zone within a reactor in the main body of which is housed the first reaction zone.

24. A process according to claim 23 wherein the reactor is partitioned into a first reaction zone forming a major proportion of the reaction space and having agitation means therein and a second smaller reaction zone having no agitation means, the second reaction zone being in liquid communication with the first reaction zone.

25. A process according to claim 1 wherein the carbon monoxide partial pressure in the first and second reaction zones is independently in the range 1 to 15 bar.

26. A process according to claim 1 wherein the carboxylic acid product is acetic acid.

* * * * *

UNITED STATES PATENT AND TRADEMARK OFFICE
CERTIFICATE OF CORRECTION

PATENT NO. : 5,932,764
DATED : August 3, 1999
INVENTOR(S) : Morris et al.

It is certified that error appears in the above-identified patent and that said Letters Patent is hereby corrected as shown below:

Column 1, line 31, delete comma "," after "carbonylating".

Column 1, line 36, delete comma "," after "feeding".

Column 2, line 7, delete open parenthesis "(" before "gases".

Column 2, line 12, delete comma "," after "subjecting".

Column 3, line 58, delete comma "," after "corresponding".

Column 5, line 10, change "chlororthenium" to --chlororuthenium--.

Column 5, line 36, delete open parenthesis "(" before "gallium".

Column 5, line 38, change "galliuim" to --gallium--.

Column 6, line 17, change "all" to --an--.

Column 8, lines 18 and 19, change "tile" to --the--.

Column 9, line 10, change "restilts" to --results--.

Signed and Sealed this

Twenty-first Day of December, 1999

Attest:

Q. TODD DICKINSON

*Attesting Officer*     *Acting Commissioner of Patents and Trademarks*